US008954160B2

United States Patent
Splett et al.

(10) Patent No.: US 8,954,160 B2
(45) Date of Patent: Feb. 10, 2015

(54) DETECTION OF EXTRACARDIAC STIMULATION BY A CARDIAC RHYTHM MANAGEMENT DEVICE

(75) Inventors: Vincent E. Splett, Apple Valley, MN (US); Robert W. Stadler, Shoreview, MN (US); Nathan A. Grenz, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 147 days.

(21) Appl. No.: 13/600,282

(22) Filed: Aug. 31, 2012

(65) Prior Publication Data

US 2013/0060298 A1 Mar. 7, 2013

Related U.S. Application Data

(60) Provisional application No. 61/530,792, filed on Sep. 2, 2011.

(51) Int. Cl.
*A61N 1/36* (2006.01)
*A61N 1/365* (2006.01)
*A61N 1/37* (2006.01)

(52) U.S. Cl.
CPC .......... *A61N 1/36585* (2013.01); *A61N 1/371* (2013.01); *A61N 1/3611* (2013.01)
USPC ............................................. 607/63; 607/27

(58) Field of Classification Search
None
See application file for complete search history.

(56) References Cited

U.S. PATENT DOCUMENTS

| 5,658,318 | A | * | 8/1997 | Stroetmann et al. | 607/6 |
| 5,814,076 | A | * | 9/1998 | Brownlee | 607/9 |
| 5,913,308 | A | * | 6/1999 | Forbes et al. | 600/513 |
| 6,772,008 | B2 | * | 8/2004 | Zhu et al. | 607/9 |
| 7,340,302 | B1 | | 3/2008 | Falkenberg | |
| 7,392,086 | B2 | | 6/2008 | Sathaye | |
| 8,165,297 | B2 | * | 4/2012 | Hoffmann | 380/256 |
| 8,209,013 | B2 | * | 6/2012 | Brooke et al. | 607/28 |
| 8,401,639 | B2 | * | 3/2013 | McCabe et al. | 607/9 |
| 2008/0071318 | A1 | | 3/2008 | Brooke | |
| 2008/0077186 | A1 | | 3/2008 | Thompson | |
| 2008/0288015 | A1 | | 11/2008 | Tehrani | |
| 2009/0054946 | A1 | | 2/2009 | Sommer | |
| 2009/0210024 | A1 | | 8/2009 | M. | |
| 2010/0114211 | A1 | * | 5/2010 | Donofrio et al. | 607/5 |
| 2010/0305637 | A1 | | 12/2010 | McCabe | |
| 2010/0305638 | A1 | | 12/2010 | McCabe | |
| 2014/0074177 | A1 | * | 3/2014 | Sathaye et al. | 607/17 |

* cited by examiner

*Primary Examiner* — Kennedy Schaetzle
(74) *Attorney, Agent, or Firm* — Michael C. Soldner

(57) ABSTRACT

A medical device system and associated method for controlling a cardiac rhythm management therapy detect extracardiac stimulation. Cardiac pacing pulses are delivered, and a cardiac electrical signal comprising myocardial depolarization and repolarization signals is acquired. A processor is configured to, responsive to the cardiac electrical signal, detect extracardiac capture due to the cardiac pacing pulse.

13 Claims, 6 Drawing Sheets

DETECTION OF EXTRACARDIAC STIMULATION BY A CARDIAC RHYTHM MANAGEMENT DEVICE

CROSS-REFERENCE TO PRIORITY APPLICATION

The present application claims priority and other benefits from U.S. Provisional Patent Application Ser. No. 61/530,792, filed Sep. 2, 2011, incorporated herein by reference in its entirety.

FIELD OF THE DISCLOSURE

The disclosure relates generally to medical devices for delivering electrical stimulation and, in particular, to an apparatus and method for detecting extracardiac stimulation by a cardiac rhythm management device.

BACKGROUND

Cardiac pacing therapies deliver pacing pulses to a patient's heart to treat various cardiac conditions, such as bradycardia, tachycardia and heart failure. Depending on the location of the cardiac pacing electrodes and the pacing pulse energy delivered, non-cardiac, excitable tissue may be inadvertently captured by the cardiac pacing pulses, causing unwanted stimulation of extracardiac nerve or muscle. For example, during cardiac resynchronization therapy (CRT), cardiac pacing pulses may be delivered to the left ventricle to restore synchrony between the right and left ventricles of the heart. The left ventricle is typically paced using electrodes carried by a transvenous lead extending through a cardiac vein along the left ventricle. These electrodes may be in proximity to portions of the phrenic nerve that innervate the diaphragm. Cardiac pacing pulses delivered to the left ventricle may inadvertently capture the phrenic nerve and thus cause diaphragm contraction. Besides phrenic nerve stimulation, intercostal muscles or other excitable tissue in proximity to a cardiac electrode may be stimulated at high enough energy to cause depolarization or "capture" of the excitable tissue, causing muscle twitching, contraction, pain or discomfort.

Extracardiac stimulation may cause pain, discomfort or annoyance to the patient. When the patient feels the extracardiac stimulation, he or she may schedule an appointment with a doctor to address the situation. A clinician will typically adjust the parameters controlling pacing pulse delivery by reprogramming the cardiac rhythm management device. In some cases, the cardiac lead may need to be repositioned in order to eliminate extracardiac stimulation. A need remains for an apparatus and method for automatically detecting extracardiac stimulation that captures non-cardiac tissue to allow the extracardiac capture to be mitigated.

DETAILED DESCRIPTION

In the following description, references are made to illustrative embodiments. It is understood that other embodiments may be utilized without departing from the scope of the disclosure. As used herein, the term "module" refers to an application specific integrated circuit (ASIC), an electronic circuit, a processor (shared, dedicated, or group) and memory that executes one or more software or firmware programs, a combinational logic circuit, or other suitable components that provide the described functionality.

Figure 1:
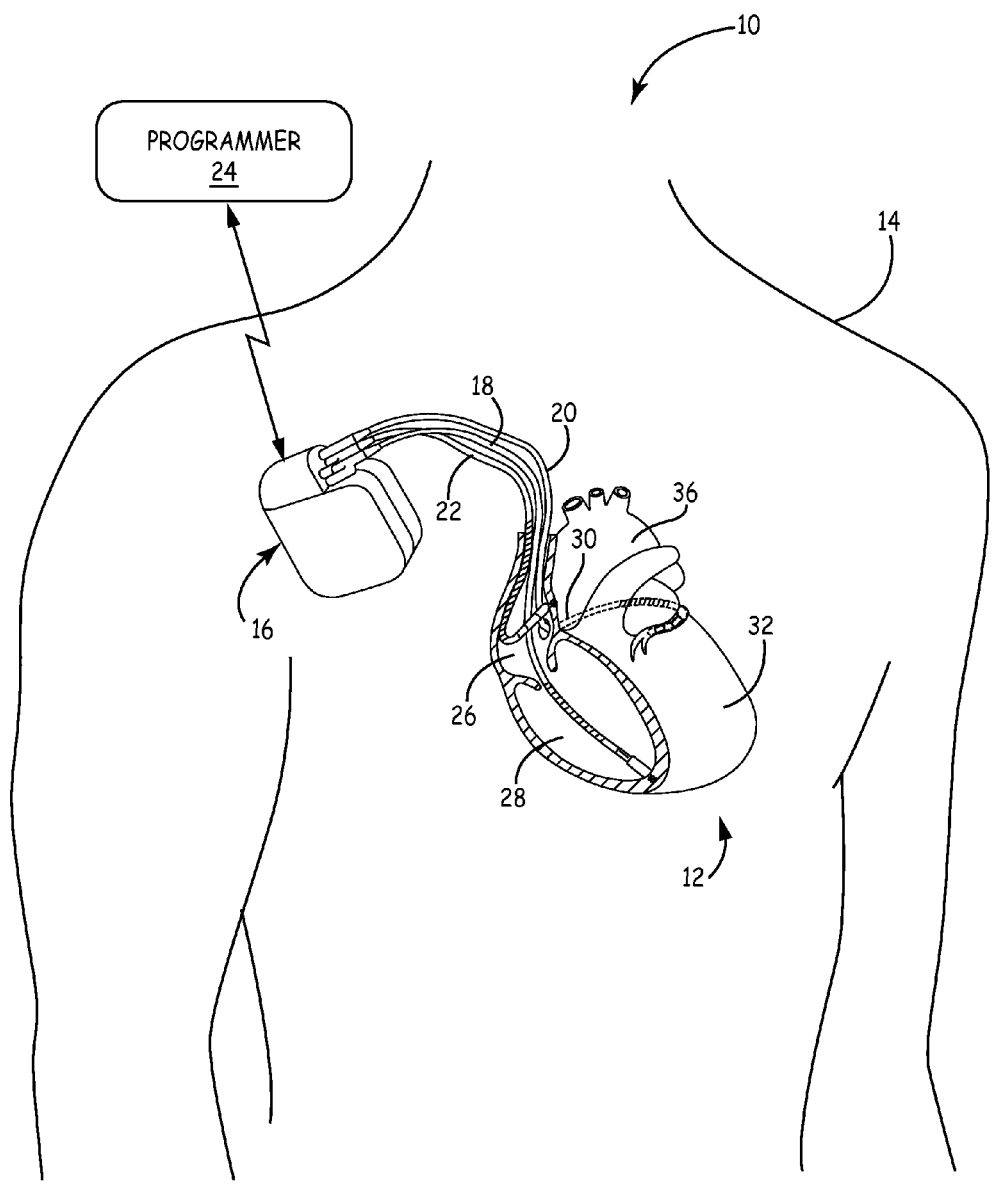
FIG. 1 is a conceptual diagram illustrating an example system that may be used to monitor and provide therapy to the heart of a patient.

FIG. 1 is a conceptual diagram illustrating an example system 10 that may be used to monitor and provide therapy to heart 12 of patient 14. System 10 includes IMD 16, which is coupled to cardiac leads 18, 20, and 22. IMD 16 is configured for wireless communication with programmer 24. IMD 16 may be, for example, an implantable pacemaker, cardioverter, and/or defibrillator that provides electrical pulses to heart 12 via electrodes coupled to one or more of leads 18, 20, and 22. IMD 16 senses cardiac electrical signals attendant to the depolarization and repolarization of the myocardium. In the embodiment shown, transvenous electrodes are used to sense cardiac electrogram (EGM) signals. In alternative embodiments, IMD 16 may be coupled to extravascular leads or electrodes that are not placed on or within the heart. For example, subcutaneous electrodes incorporated along a housing of IMD 16 or carried by subcutaneous or submuscular leads extending from IMD 16 may be used to sense electrocardiogram (ECG) signals. EGM and/or ECG signals are referred to collectively herein as "cardiac electrical signals" and may include signals corresponding to the depolarization of the atria, i.e. P-waves, and/or the depolarization and repolarization of the ventricles, i.e. QRS and T-wave signals. Cardiac electrical signals are used by IMD 16 in accordance with the methods described herein for detecting extracardiac capture of excitable tissue. Alerts or reports based thereon may be transmitted to programmer 24 via wireless telemetry.

Leads 18, 20, 22 extend into the heart 12 of patient 14 to sense electrical activity of heart 12 and deliver electrical stimulation to heart 12. In the example shown in FIG. 1, right ventricular (RV) lead 18 extends into right ventricle 28 for pacing and sensing in the RV. Left ventricular (LV) coronary sinus lead 20 extends into a cardiac vein via the coronary sinus 30 to a region adjacent to the free wall of left ventricle 32 for pacing and sensing in the LV. Right atrial (RA) lead 22 extends into the right atrium 26 for pacing and sensing in the right atrium. In some embodiments, coronary sinus lead 20 may additionally include electrodes positioned adjacent left atrium (LA) 36 for sensing and pacing in the LA.

IMD 16 provides pacing pulses to heart 12 based on the electrical signals sensed within heart 12. The configurations of electrodes used by IMD 16 for sensing and pacing may be unipolar or bipolar, including "combipolar" combinations that use two or more electrodes tied together to serve as a cathode or anode. IMD 16 may also provide defibrillation therapy and/or cardioversion therapy via electrodes located on at least one of the leads 18, 20, 22.

Programmer 24 may be a handheld device or a microprocessor based home monitor or bedside programming device used by a clinician. IMD 16 and programmer 24 communicate via wireless communication. Examples of communication techniques may include, for example, low frequency or radiofrequency (RF) telemetry using Bluetooth or MICS but other techniques are also contemplated.

A user, such as a physician, technician, or other clinician, may interact with programmer 24 to communicate with IMD 16. For example, the user may interact with programmer 24 to retrieve physiological or diagnostic information from IMD 16. Programmer 24 may receive signals from IMD 16 corresponding to a notification or alert that extracardiac stimulation has been detected. A user may also interact with programmer 24 to program IMD 16, e.g., select values for operational parameters of the IMD. For example, a user interacting with programmer 24 may select programmable parameters controlling a cardiac rhythm management therapy delivered to the heart 12 via any of leads 18, 20 and 22.

While not shown explicitly in FIG. 1, it is contemplated that a user may interact with programmer 24 remotely via a communications network by sending and receiving interrogation and programming commands via the communications network. Programmer 24 may be coupled to a communications network to enable a clinician using a computer to access data received by programmer 24 and to transfer programming instructions to programmer 24, which in turn programs IMD 16. Reference is made to commonly-assigned U.S. Pat. No. 6,599,250 (Webb et al.), U.S. Pat. No. 6,442,433 (Linberg et al.) U.S. Pat. No. 6,622,045 (Snell et al.), U.S. Pat. No. 6,418,346 (Nelson et al.), and U.S. Pat. No. 6,480,745 (Nelson et al.) for general descriptions and examples of network communication systems for use with implantable medical devices for remote patient monitoring and device programming, hereby incorporated herein by reference in their entirety.

Figure 2:
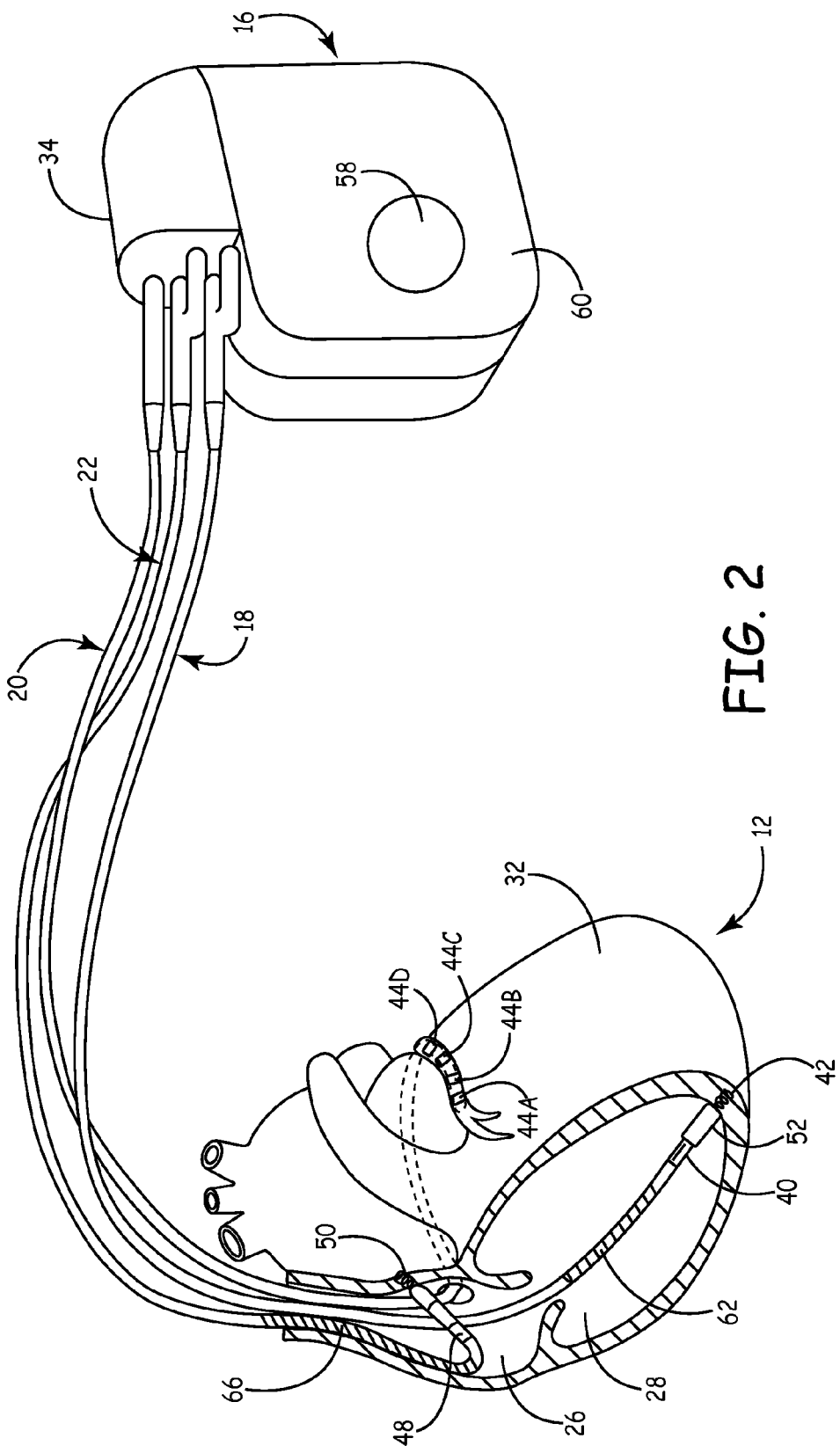
FIG. 2 is a conceptual diagram illustrating the implantable medical device (IMD) and leads of FIG. 1 in greater detail.

FIG. 2 is a conceptual diagram illustrating IMD 16 and leads 18, 20, and 22 of system 10 in greater detail. Leads 18, 20, 22 are electrically coupled to a signal generator and a sensing module enclosed within housing 60 of IMD 16 via connector block 34. Each of the leads 18, 20, 22 includes an elongated insulative lead body carrying one or more conductors coupled to individual electrodes of the respective lead for electrically coupling IMD 16 to the RA 26, RV 28 and LV 32. RV pacing and sensing electrodes 40 and 42 are located adjacent a distal end of lead 18. RA pacing and sensing electrodes 48 and 50 are located adjacent to a distal end of RA lead 22. In some example configurations, lead 20 is a multipolar lead and is shown in FIG. 2 as a quadripolar lead including four electrodes, namely electrodes 44A-44D, which are located adjacent to a distal end of lead 20 for sensing and pacing in the LV. In other embodiments, lead 20 may include more or fewer electrodes.

Leads 18 and 22 are also shown to include RV coil electrode 62 and superior vena cava (SVC) coil electrode 66, respectively, which are typically used for delivering high voltage cardioversion or defibrillation pulses. In alternative embodiments, lead 18 may carry both coil electrodes 62 and 66. Coil electrodes 62 and 66 may be used in combination with other available electrodes for sensing cardiac electrical signals in some embodiments. Each of the electrodes 40, 42, 44A-44D, 48, 50, 62, and 66 is electrically coupled to a respective one of the conductors within the lead body of its associated lead 18, 20, 22, and thereby individually coupled to an electrical pulse generator and/or cardiac sensing module of IMD 16.

IMD 16 may include one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward surface of housing 60. Other division between insulated and uninsulated portions of housing 60 may be employed to define two or more housing electrodes. In some examples, housing electrode 58 comprises substantially all of housing 60. Housing electrode 58 may be paired with another available electrode used to sense cardiac electrical signals and may be used with another cardiac electrode for delivering unipolar pacing pulses.

IMD 16 senses cardiac electrical of heart 12 via one or more unipolar or bipolar sensing electrode pairs selected from electrodes 40, 42, 44A-44D, 48, 50, 58, 62, and 66. IMD 16 delivers pacing pulses via any bipolar, unipolar or combipolar combination of electrodes 40, 42, 44A-44D, 48, 50, 58, 62, and 66 to produce depolarization of cardiac tissue of heart 12. For example, electrodes 40, 42, and may be used to deliver bipolar RV pacing to heart 12. Electrodes 44A-44D may be used to deliver bipolar LV pacing to heart 12, and electrodes 48 and 50 may be used to deliver bipolar RA pacing to heart 12. IMD 16 may deliver cardioversion or defibrillation pulses to heart 12 via any combination of coil electrodes 62 and 66 and housing electrode 58.

The configuration of therapy system 10 illustrated in FIGS. 1 and 2 is merely one example. IMD system 10 may include any suitable number of leads coupled to IMD 16 and extending to any location within or proximate to heart 12. In other examples, a cardiac rhythm management system may include epicardial electrodes, subcutaneous or submuscular electrodes or other extravascular electrodes instead of or in addition to the transvenous leads 18, 20, 22 illustrated in FIGS. 1 and 2. Furthermore, IMD 16 need not be implanted within patient 14. In examples in which IMD 16 is not implanted in patient 14, IMD 16 may deliver electrical pacing pulses to heart 12 via percutaneous leads that extend through the skin of patient 14 to a variety of positions within or outside of heart 12.

Two or more electrodes, and the polarity of the electrodes, define a vector, or path, for delivering pacing pulses to heart 12. When multiple electrodes are positioned within or along heart 12, there are numerous vectors that may be used to deliver pacing pulses to heart 12. For example, various combinations of the electrodes on a single quadripolar lead, i.e., a lead with four electrodes on the lead, such as lead 20, as well as unipolar combinations of the lead electrodes with a housing electrode or, for example, a coil electrode, may provide numerous different vectors that may be used to deliver pacing pulses to a particular chamber of heart 12 that the lead is within or on. IMD 16 may be configured to automatically select a different pacing vector in response to detecting extracardiac stimulation using sensed cardiac electrical signals. Additionally or alternatively, other parameters controlling the pacing pulse delivery, such as pulse amplitude, pulse width, and pulse shape may be adjusted to mitigate extracardiac capture of excitable tissue.

Figure 3:
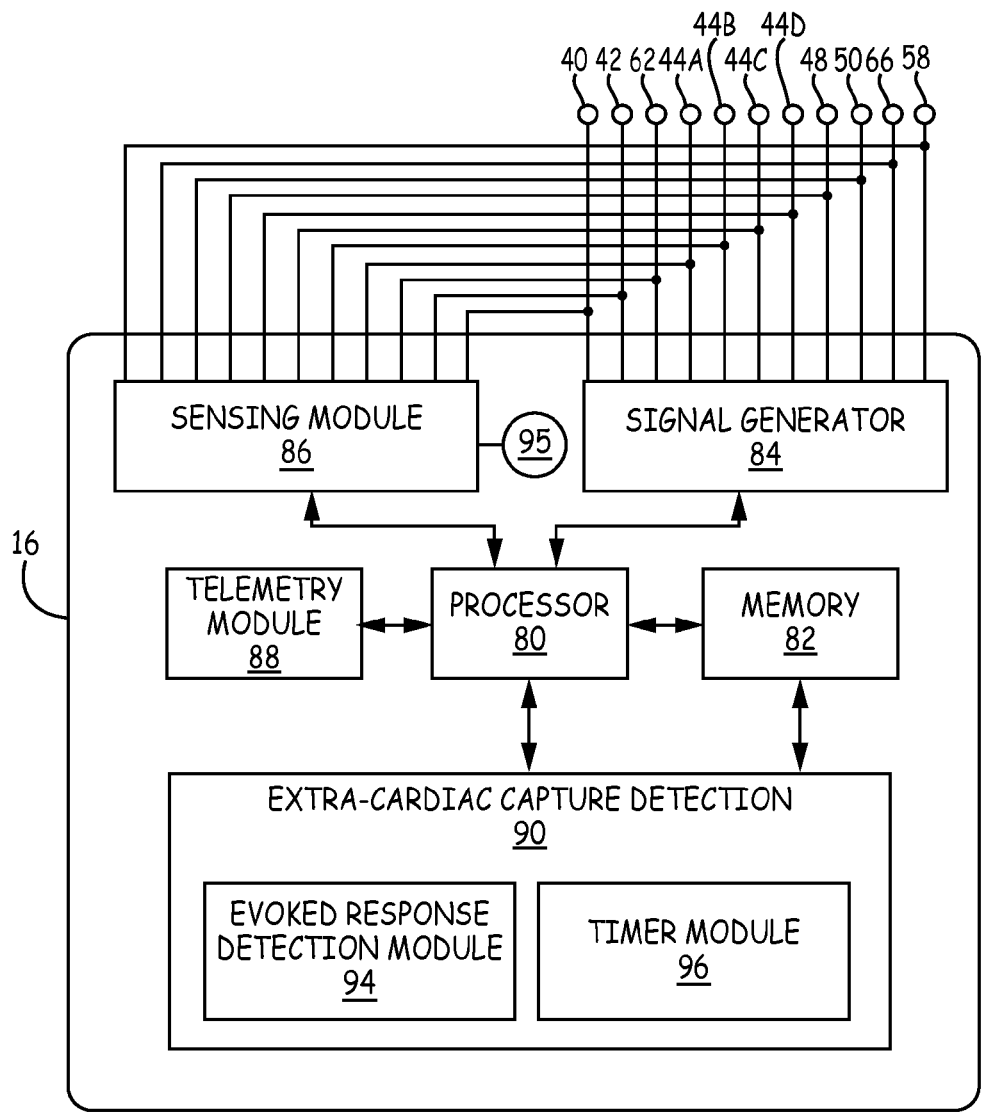
FIG. 3 is a functional block diagram illustrating one example configuration of the IMD of FIG. 2.

FIG. 3 is a functional block diagram illustrating one example configuration of IMD 16. In the example illustrated by FIG. 3, IMD 16 includes a processor 80, memory 82, signal generator 84, sensing module 86, and telemetry module 88. IMD 16 further includes extracardiac capture detection module 90, which itself includes evoked response detection module 94 and timer module 96 for detecting capture of non-cardiac excitable tissue.

Memory 82 may include computer-readable instructions that, when executed by processor 80, cause IMD 16 and processor 80 to perform various functions attributed throughout this disclosure to IMD 16, processor 80, and extracardiac capture detection module 90. The computer-readable instructions may be encoded within memory 82. Memory 82 may comprise computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof. In one example, extracardiac capture detection module 90, evoked response detection module 94, and timer module 96 may, at least in part, be stored or encoded as instructions in memory 82 that are executed by processor 80.

Processor 80 controls signal generator 84 to deliver stimulation therapy, e.g., cardiac pacing or cardiac resynchronization therapy (CRT), to heart 12 according to a selected one or more therapy programs, which may be stored in memory 82. Signal generator 84 is electrically coupled to electrodes 40, 42, 44A-44D, 48, 50, 58, 62, and 66, e.g., via conductors of the respective lead 18, 20, 22, or, in the case of housing electrode 58, via an electrical conductor disposed within housing 60 of IMD 16. Signal generator 84 is configured to generate and deliver electrical stimulation therapy to heart 12 via selected combinations of electrodes 40, 42, 44A-44D, 48, 50, 58, 58, 62, and 66. Signal generator 84 is configured to deliver cardiac pacing pulses according to any programmed cardiac rhythm management therapy, such as bradycardia pacing, anti-tachycardia pacing, CRT or other therapy, using selected unipolar or bipolar pacing vectors.

Signal generator 84 may include a switch module (not shown) and processor 80 may use the switch module to select, e.g., via a data/address bus, which of the available electrodes are used to deliver pacing pulses. Processor 80 may also control which of electrodes 40, 42, 44A-44D, 48, 50, 58, 62, and 66 is coupled to signal generator 84 for delivering stimulus pulses, e.g., via the switch module. The switch module may include a switch array, switch matrix, multiplexer, or any other type of switching device suitable to selectively couple a signal to selected electrodes.

Sensing module 86 monitors signals from at least one pair of electrodes 40, 42, 44A-44D, 48, 50, 58, 62, or 66 in order to monitor electrical activity of heart 12. Sensing module 86 may also include a switch module to select which of the available electrodes are used to sense the cardiac activity. In some examples, processor 80 selects the electrodes that function as sense electrodes, or the sensing vector, via the switch module within sensing module 86.

In particular, sensing module 86 is coupled to a selected sensing electrode combination for detecting an evoked response of extracardiac tissue subsequent to the delivery of a cardiac pacing pulse. The sensing electrode pair that provides an optimal cardiac electrical signal for use in detecting extracardiac tissue capture may be selected by a switch included in electrical sensing module during extracardiac evoked response sensing timing windows. The optimal sensing electrode pair for detecting extracardiac capture may be identified as an electrode pair providing the highest signal-to-noise ratio of an evoked response known to be associated with extracardiac capture relative to the cardiac signal baseline.

Sensing module 86 includes multiple detection channels, each of which may be selectively coupled to respective combinations of electrodes 40, 42, 44A-44D, 48, 50, 58, 62, or 66 to detect electrical activity of a particular chamber of heart 12. Each detection channel may comprise an amplifier that outputs an indication to processor 80 in response to sensing of a cardiac depolarization, in the respective chamber of heart 12. In this manner, processor 80 may detect the occurrence of R-waves and P-waves in the various chambers of heart 12. In accordance with the disclosed methods, any of the existing detection channels and/or one or more dedicated extra detection channels may be provided for detecting extracardiac capture. If pacing pulses are being delivered to more than one cardiac chamber or location, for example if dual chamber, biventricular, or multi-chamber pacing is being delivered, extracardiac capture could be occurring in more than one location. As such, one or more cardiac electrical signals may be acquired for detecting extracardiac capture that may be occurring at multiple locations.

Memory 82 stores intervals, counters, or other data used by processor 80 to control the delivery of pacing pulses by signal generator 84. Such data may include intervals and counters used by processor 80 to control the delivery of pacing pulses to one or more cardiac chambers according to a pacing therapy. The intervals and/or counters are, in some examples, used by processor 80 to control the timing of delivery of pacing pulses relative to an intrinsic or paced event, e.g., in another chamber. Memory 82 may additionally store intervals or windows set for sensing events from a cardiac electrical signal. In one embodiment, an extracardiac capture sensing window is set relative to a delivered pacing pulse.

Extracardiac capture detection module 90 uses signals from sensing module 86 to detect capture of non-cardiac excitable tissue when signal generator 84 delivers a pacing pulse. Via the switching module, processor 80 may control which of electrodes 40, 42, 44A-44D, 48, 50, 58, 62, and 66 is coupled to sensing module 86 to sense cardiac depolarization signals for use in determining a need for therapy, controlling the timing for delivering cardiac pacing pulses, and sensing a cardiac signal for detecting evoked responses corresponding to capture of non-cardiac excitable tissue.

Memory 82 may store predetermined intervals or voltage thresholds which define whether a detected signal has an adequate magnitude and is appropriately timed relative to the pacing pulse to be considered a depolarization in a cardiac chamber indicative of capture or an evoked response in the myocardium or to be considered a depolarization in non-cardiac tissue due to extracardiac capture. In some examples, a channel of sensing module 86 used to detect extracardiac capture comprises a sense amplifier which provides an indication to processor 80 when a cardiac electrical signal has an adequate magnitude or other circuitry for detecting an extracardiac evoked response signal feature indicative of a non-cardiac depolarization and therefore useful in detecting extracardiac capture.

IMD 16 may include one or more additional physiological sensors 95, incorporated within or on the IMD housing 60 or carried by a lead extending from IMD 16. Sensor(s) 95 are coupled to sensing module 86 and may be used in conjunction with extracardiac capture detection algorithms. For example, a posture or activity sensor may be included in sensor 95 to monitor the patient's physical activity level and/or posture. Extracardiac capture may be more likely to occur during particular patient postures or activities due to movement or shifting of pacing electrodes relative to extracardiac excitable tissue. As such, detection of a change in posture or activity may trigger an extracardiac capture detection algorithm or this information may be included in a report transmitted to programmer 24 for alerting a clinician to the occurrences of extracardiac stimulation.

In some embodiments a respiration signal is acquired for gating cardiac electrical signals used for non-cardiac evoked response signal detection. Capture of non-cardiac excitable tissue, such as the phrenic nerve or intercostal muscles, may be more likely to occur during a particular respiration phase due to shifting of the pacing electrodes relative to the patient's anatomy during respiratory motion. Averaging a cardiac electrical signal over multiple consecutive cardiac cycles may filter non-cardiac evoked response signals that may be present on some cardiac cycles that occur during a particular phase of respiration, e.g. inspiration or expiration or portions thereof, but not all cardiac cycles. As such, sensor(s) 95 may include a sensor responsive to patient respiration, such thoracic impedance electrodes or an accelerometer. Alternatively, an impedance signal or a cardiac electrical signal sensed using any of electrodes 40, 42, 44A-D, 48, 50, 58, 62 and 66 may be low pass filtered for obtaining a cyclical signal correlated to the respiration cycle. As will be described further herein, a respiration signal acquired by sensing module 86 from sensor(s) 95 and/or electrodes 40, 42, 44A-D, 48, 50, 58, 62, and 66 may be used to gate cardiac electrical signal sensing to the respiration cycle to facilitate detection of non-cardiac evoked response signals that occur during particular respiration phases.

Extracardiac capture detection module 90, in the example of FIG. 3, is capable of detecting capture of non-cardiac excitable tissue during delivery of a cardiac pacing therapy. Extracardiac capture detection module 90 uses a timer module 96 in some embodiments to determine when to detect a non-cardiac evoked response relative to a pacing pulse, a cardiac evoked response or depolarization signal (P-wave or R-wave) or a respiration cycle. Extracardiac capture detection module 90 includes an evoked response detection module 94 for detecting a non-cardiac evoked response using signal averaging, signal differences, peak detection, peak tracking, or other signal analysis and detection methods described herein. Evoked response detection module 94 may include appropriate circuitry and/or programmed instructions for executing a signal processing and detection algorithm.

Processor 80 may determine pacing capture thresholds for each of a plurality of pacing vectors according to various capture measurement methods for use in selecting a pacing vector used to deliver a cardiac rhythm management therapy. Extracardiac capture detection may be performed in conjunction with cardiac pacing capture threshold measurements and extracardiac capture detection results may be used in selecting a pacing vector and pacing pulse amplitude or pulse width. In other words, as a pacing pulse energy is varied to determine a threshold amplitude or width, extracardiac capture detection module 90 may be enabled to determine if a non-cardiac evoked response is detected and that information may be stored with the cardiac capture threshold for a particular pacing electrode vector.

Figure 4:
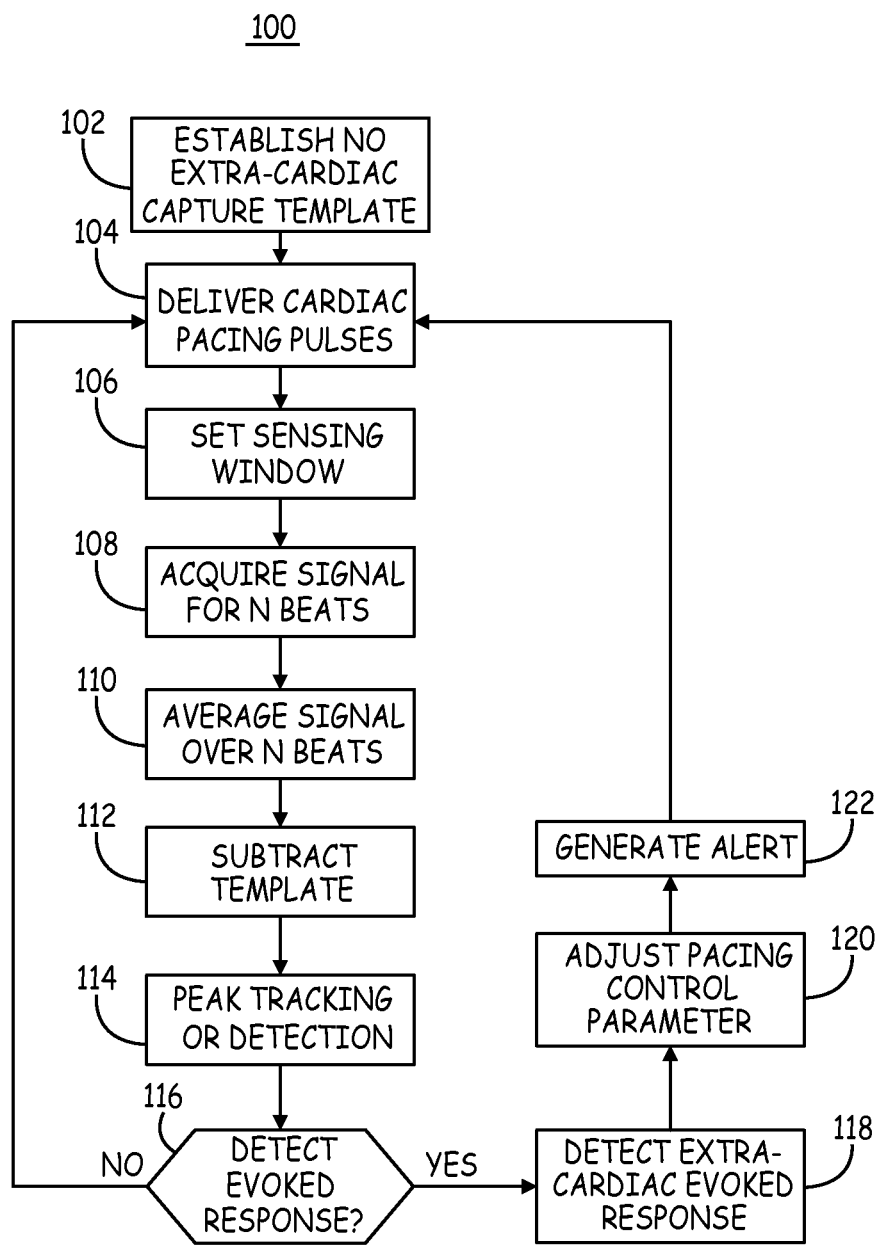
FIG. 4 is a flow chart of a method for detecting extracardiac capture according to one embodiment.

FIG. 4 is a flow chart 100 of a method for detecting extracardiac capture according to one embodiment. Flow chart 100 and other flow charts presented herein are intended to illustrate the functional operation of the device, and should not be construed as reflective of a specific form of software or hardware necessary to practice the methods described. It is believed that the particular form of software and/or hardware will be determined primarily by the particular system architecture employed in the device and by the particular sensing and therapy delivery methodologies employed by the device. Providing software and/or hardware to accomplish the described functionality in the context of any modern IMD, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 102, a cardiac electrical signal template is established representing a signal when no extracardiac capture is present. The template is established using a cardiac electrical signal acquired from a sensing electrode pair that will also be used for detecting extracardiac evoked responses and provides a baseline comparison for detecting signal changes arising from an extracardiac evoked response. In various embodiments, a sensing electrode pair may be an RVtip-to-RVring, RVtip-to-RVcoil, LVtip-to-RVcoil, RVring-to-housing electrode or any other available sensing electrode pair.

The no extracardiac capture signal template may be established at block 102 during cardiac pacing at a pacing pulse amplitude and width that is known to capture the heart and known not to cause extracardiac capture. For example, EGM or ECG signals may be acquired for multiple cardiac paced cycles when a clinician or the patient verifies that no extracardiac capture is present. To illustrate, if a cardiac pacing threshold is 1 V, cardiac pacing may be delivered at or above the cardiac pacing threshold, for example at approximately 1.5 V. After verifying no extracardiac capture is occurring, the EGM/ECG signal is acquired for multiple cardiac cycles and averaged to obtain a template at block 102.

The EGM or ECG signal used to establish the template may be acquired during a sensing window defined relative to the pacing pulse. The sensing window corresponds to an expected time of a non-cardiac evoked response. The depolarization of non-cardiac excitable tissue is expected to occur within approximately 5 ms to 30 ms following a pacing pulse. The QRS complex corresponding to cardiac depolarization following a pacing pulse typically occurs at least 50 ms after the pacing pulse or later. As such, a sensing window for detecting a non-cardiac evoked response may extend between a pacing pulse and a QRS signal, e.g. between a pacing pulse and up to approximately 40 to 50 ms after the pacing pulse. The sensing window may start upon pacing pulse delivery or may begin just before or just after the pacing pulse. For example, the sensing window may begin anytime between approximately 10 ms before and 10 ms after the pacing pulse and end approximately 40 to 50 ms after the pacing pulse.

In other embodiments, the no extracardiac capture template may be established during cardiac pacing at a pacing pulse amplitude and width that is below the cardiac capture threshold. A sub-threshold cardiac pacing pulse that does not capture the heart is not expected to capture extracardiac tissue (though in some rare circumstances extracardiac capture may occur when cardiac capture does not). The EGM/ECG may be acquired during subthreshold cardiac pacing for multiple cardiac cycles and ensemble averaged over the cardiac cycle to obtain the no extracardiac capture template.

In other embodiments, a cardiac electrical signal template representing no extracardiac capture may be established during no cardiac pacing (or pacing at 0 V). In this case, verification of no extracardiac capture is not required since no pacing pulses are being delivered. However, the EGM/ECG signal during no cardiac pacing may differ somewhat from the cardiac electrical signal during cardiac pacing. A no extracardiac capture template established during no cardiac pacing may not provide as great of sensitivity when used as a baseline for detecting extracardiac evoked responses as a template established during cardiac pacing.

At block 104, cardiac pacing pulses are delivered. Pacing may be delivered to deliver a therapy according to programmed therapy control parameters. Alternatively, pacing may be delivered according to a cardiac capture threshold test or according to an intermittently applied extracardiac capture detection algorithm. A sensing window for detecting a noncardiac evoked response is set at block 106. The sensing window is scheduled as described above and extends from approximately ±10 ms of the pacing pulse up to approximately 50 ms after the pacing pulse. In one embodiment, the window extends from the pacing pulse until 30 ms after the pacing pulse.

At block 108, the EGM or ECG signal is acquired during the sensing window for a desired number (N) of cardiac cycles. The signal may be acquired, for example, for 5, 10, 20, 30, or more cardiac cycles. At block 110, the EGM or ECG signal is averaged over the N cardiac cycles. The established template corresponding to no extracardiac capture is subtracted from the averaged signal at block 112. This averaged signal difference provides a greater signal-to-noise ratio of the non-cardiac evoked response signal when it is present and enables detection of extracardiac capture.

At blocks 114 and 116, analysis of the averaged signal difference is performed to detect an evoked response signal. In one example, peak tracking is performed at block 114. If a tracked peak during the sensing window exceeds a predetermined evoked response detection threshold, an extracardiac evoked response is detected at decision block 116 and extracardiac capture is detected at block 118.

In another example, negative peak tracking is performed at block 114. When no extracardiac evoked response is present during the sensing window, the negative peak tracking detects a decaying signal that reaches baseline corresponding to the decaying pacing pulse signal deflection. If negative peak tracking detects a threshold deviation from the monotonically decaying pacing pulse deflection during the sensing window, an evoked response is detected at block 116 as evidence of extracardiac capture.

In other embodiments, the averaged signal difference may be analyzed using a peak amplitude measurement, peak-to-peak amplitude difference, slope, area under the signal, threshold crossing, signal width, or other signal feature for detecting the evoked response signal during the sensing window.

Figure 5:
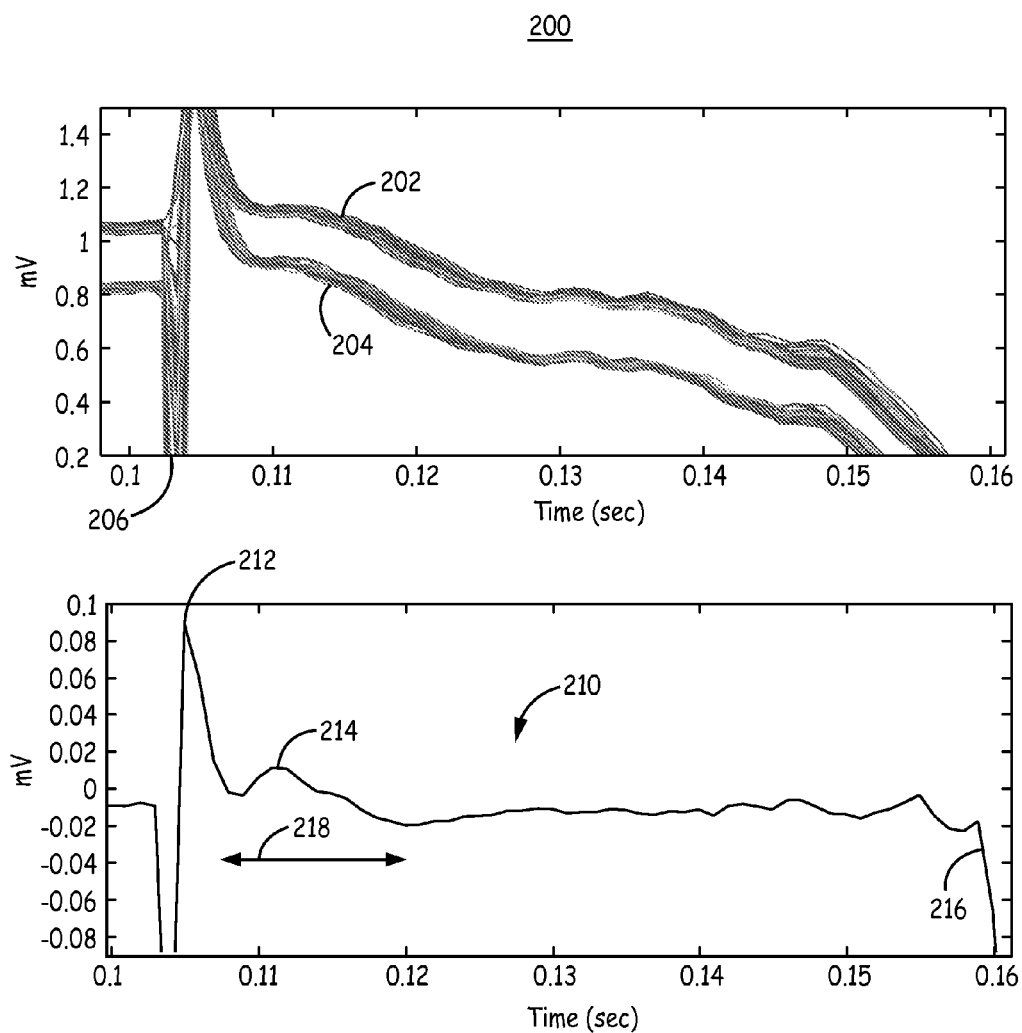
FIG. 5 is a series of plots of cardiac EGM signals acquired during cardiac pacing with and without extracardiac capture.

In some embodiments, signal averaging and/or template subtraction is not performed and the evoked response detection analysis is performed on the EGM/ECG signal on a beat-by-beat basis and/or without subtracting the no extracardiac capture template. However, as shown in FIG. 5 below, signal averaging and subtraction of a template corresponding to no extracardiac capture can improve the non-cardiac evoked response signal-to-noise ratio in the cardiac electrical signal.

If extracardiac capture is not detected, i.e. no evoked response is detected at block 116, the therapy continues being delivered according to currently programmed values at block 104. If extracardiac capture is detected at block 118, the IMD may automatically adjust a pacing therapy control parameter at block 120. For example, the pacing pulse amplitude, pulse width, pulse shape, or pacing electrode vector may be changed. In some embodiments, a clinician may program two or more pacing electrode vectors in order of preference, for example a first choice, second choice and so on. The IMD begins delivering therapy using the first choice. If extracardiac capture is detected by the IMD automatically, the IMD switches to the next pacing electrode vector selection programmed by the clinician at block 120. If all of the programmed selections have been attempted, an alert may be generated at block 122.

Additionally or alternatively to adjusting a control parameter, an alert may be generated at block 122 to be transmitted to an external device to notify a clinician or other user that the patient's IMD has been or needs to be reprogrammed to avoid extracardiac capture. An alert transmitted to a programmer or home monitoring device that is coupled to a communication network may be transmitted further to a remote patient management database, clinician computer, or other communication device in a hospital or clinic.

The therapy is delivered at block 104 using adjusted control parameters. In some embodiments, the therapy may be temporarily withheld in response to detecting extracardiac capture. If the therapy is a non-critical therapy, temporary cessation of the therapy may allow the clinician time to perform or enable IMD reprogramming, either remotely or in a clinic.

FIG. 5 is a series of plots 200 of cardiac EGM signals acquired during cardiac pacing with and without extracardiac capture. The EGM signals were sensed using an RVtip-RV-coil sensing vector during bipolar pacing in the LV. EGM signals 202 represent signals sensed over thirty cardiac cycles during LV pacing at 2.0 Volts pulse amplitude with no extracardiac capture present. EGM signals 204 represent signals sensed over thirty cardiac cycles during LV pacing at 3.0 Volts with extracardiac (phrenic nerve) capture present. Both signals 202 and 204 correspond to cardiac capture (suprathreshold) pacing. A large deflection 206 corresponds to the pacing pulse.

In the lower panel, the averaged signal difference 210 is shown. Averaged signal difference is the difference between the average of signals 202 and the average of signals 204. A large deflection 212 corresponds to the pacing pulse signal. An extracardiac evoked response signal 214 is observed as a relatively smaller deflection following the pacing pulse deflection 212. The QRS complex 216 is observed as a relatively larger deflection occurring later than evoked response 214 after the pacing pulse 212. The averaged signal difference 210 provides enhanced signal-to-noise ratio of the extracardiac evoked response signal 214 occurring in the cardiac EGM signals 204.

An evoked response detection algorithm is applied to the averaged signal difference 210 which includes analyzing the signal difference 210 during a sensing window 218 set between the pacing pulse signal 212 and the QRS signal 216. In the example shown, window 218 extends from approximately 7 ms to approximately 20 ms after pacing pulse signal 212. As discussed previously, a positive peak tracking, negative peak tracking, threshold comparison, slope, area under the signal, or other aspect for positively identifying evoked response signal 214 may be included in the analysis for detecting evoked response signal 214.

Figure 6:
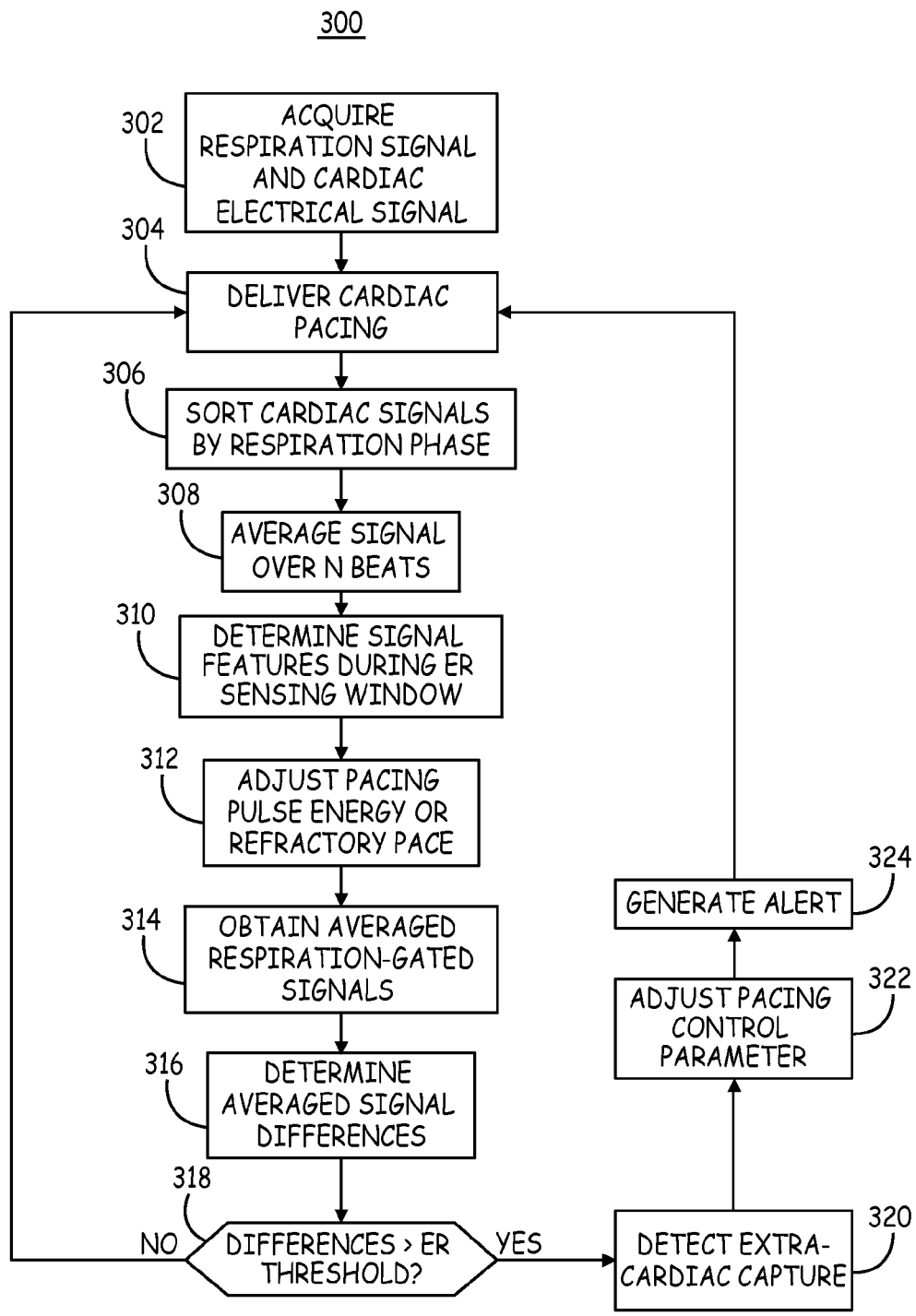
FIG. 6 is a flow chart 300 of an alternative method for detecting extracardiac capture.

FIG. 6 is a flow chart 300 of an alternative method for detecting extracardiac capture. At block 302, a respiration signal and a cardiac electrical signal are acquired by the IMD sensing circuitry. The respiration signal may be acquired from a dedicated respiration sensor or filtered from the cardiac electrical signal, a cardiac impedance signal or other signal that is responsive to the respiration cycle.

It is anticipated that the methods disclosed in conjunction with flow charts presented herein will be implemented in an implantable medical device receiving signals at block 302 from implanted sensors, which may include both cardiac electrodes and a respiration sensor. However, it is contemplated that the disclosed extracardiac capture detection methods may be implemented in systems that include at least some external components. For example, external ECG electrodes may be used with an external sensing module receiving the ECG signals for processing by an implanted or external processor.

At block 304, a cardiac pacing is delivered. The cardiac pacing may be delivered according to a programmed therapy, such as bradycardia pacing or CRT. Alternatively, the cardiac pacing delivered at block 304 may be delivered according to a test protocol not intended or optimized to have a particularly therapeutic benefit. For example, cardiac pacing pulses may be delivered in the LV using a candidate pacing electrode pair that may be selected for use during CRT, however these pacing pulses may not be optimized for timing relative to the atria or the RV to provide maximum CRT benefits. Pacing pulses may be delivered at nominal timing intervals for the purposes of testing whether extracardiac capture is present and would be likely to be present during a cardiac therapy that uses the candidate pacing vector.

As such, the methods described herein for detecting extracardiac capture may be performed for diagnostic purposes to determine electrode vectors and pacing pulse energies that will likely result in extracardiac capture. This information can be used to select programmable control parameters used for delivering a cardiac rhythm management therapy. Additionally or alternatively, the methods described herein may be executed during the delivery of a cardiac rhythm management therapy, either continuously or intermittently, for detecting extracardiac capture and responding appropriately.

At block 306, cardiac electrical signals are sorted, on a beat-by-beat basis, according to the respiration cycle phase during which the cardiac cycle occurred. Various techniques could be used to acquire or group cardiac cycles according to timing within the respiration cycle. For example, cardiac signal sensing could be gated relative to a detected event or feature of the respiration cycle, such as peak inspiration or peak expiration. Alternatively, cardiac signals may be acquired continuously then sorted according to relative time of a pacing pulse or sensed P-waves or R-waves to a fiducial point of the respiration cycle, e.g. marking the onset, offset, or peak of inspiration or expiration. Cardiac signals may be gated or sorted according to one or more respiration cycle phases such as early, mid and late inspiration and early, mid and late expiration or any combination thereof.

Cardiac electrical signals acquired during a particular phase of the respiration cycle are averaged over a desired number of cardiac cycles (N) to obtain an averaged signal corresponding to the particular respiration phase. In some embodiments, an averaged signal difference between this respiration-gated, averaged signal and a no extracardiac capture template may be determined to enable evoked response detection as generally described in conjunction with FIG. 4.

In an alternative embodiment, as shown in FIG. 6 signal features during an extracardiac evoked response sensing window are determined from the respiration-gated, averaged signal at block 310. These features may be compared to thresholds or ranges for detecting an extracardiac evoked response.

In the example shown, the pacing pulse energy is adjusted and/or refractory pacing pulses are delivered at block 312. The pacing pulse amplitude or width may be adjusted and the process of obtaining respiration-gated, average cardiac signals is repeated for the adjusted pulse energy. The averaged signal difference between two different pacing pulse energies acquired during the same respiration phase is determined at block 316. If this difference is greater than an evoked response detection threshold (block 318), extracardiac capture is detected at block 320.

If the pacing pulse amplitude or width is reduced at block 312, the extracardiac evoked response may get smaller or disappear, resulting in a detectable difference in the respiration-gated, averaged signal differences (block 316) and confirming the presence of non-cardiac capture. In some cases, if the pacing pulse amplitude or width is increased, the extracardiac evoked response may also increase due to greater recruitment of nerve or muscle fibers. As such, a threshold change in the averaged signal after adjusting pacing pulse energy relative to the initially measured averaged signal (blocks 308 and 310) can be used to confirm extracardiac capture at the initial pacing pulse energy.

In some embodiments, the pacing pulse timing may be adjusted so that pacing pulses are delivered during absolute refractory of the myocardium or a second pacing pulse may be added during myocardial absolute refractory at block 312. A comparison between the original averaged signal and an averaged signal obtained during refractory pacing can also be used to verify extracardiac capture at block 318. The refractory pace may be delivered to determine if a similar signal occurs a second time during a paced cardiac cycle confirming a non-cardiac evoked response. Alternatively, the refractory pace may be delivered with a different pulse energy to confirm an expected change in an extracardiac evoked response to the refractory pacing pulse as compared to the non-refractory pacing pulse delivered during the same cardiac cycle.

These evoked response signal detection and confirmation methods may be performed for cardiac signals acquired during one respiration phase, e.g. peak inspiration, or repeated for multiple respiration phases, e.g. peak inspiration and peak expiration. If extracardiac capture is detected at block 320, pacing control parameter may be adjusted at block 320 and/or an alert may be generated at block 324 as described previously.

It is understood that the operations performed as described in conjunction with flow charts presented herein may be performed in a different order or combination than the particular order and combinations presented herein. For example, operations described in conjunction with flow chart 300 may be combined with operations described in conjunction with flow chart 200. Furthermore, operations may be omitted or added to achieve non-cardiac evoked response detection in the manner generally disclosed herein.

Thus, an apparatus and method for detecting extracardiac capture in a cardiac rhythm management device have been presented in the foregoing description with reference to specific embodiments. It is appreciated that various modifications to the referenced embodiments may be made without departing from the scope of the disclosure as set forth in the following claims.

The invention claimed is:

1. A method for controlling a cardiac rhythm management therapy, comprising:
    delivering a cardiac pacing pulse;
    acquiring a cardiac electrical signal comprising myocardial depolarization and repolarization signals; and
    enabling a processor to, responsive to the cardiac electrical signal, detect extracardiac capture due to the cardiac pacing pulse, the method further comprising:
        acquiring the cardiac signal for a plurality of paced cardiac cycles;

averaging the cardiac signals acquired for the plurality of paced cardiac cycles to obtain an averaged signal; and detecting the extracardiac capture from the averaged signal.

2. The method of claim 1, further comprising
establishing a cardiac signal template comprising no extracardiac stimulation; and
detecting the extracardiac capture from a difference between the averaged signal and the template.

3. The method of claim 1, further comprising:
sensing a respiration signal; and
gating the cardiac electrical signal according to a phase of the respiration signal.

4. The method of claim 1, further comprising adjusting a parameter controlling the pacing pulse in response to detecting the extracardiac stimulation.

5. The method of claim 4, wherein the parameter comprises one of a timing parameter and an electrode selection parameter.

6. The method of claim 1, further comprising generating an alert notification in response to detecting the extracardiac stimulation.

7. An implantable medical device system for delivering a cardiac rhythm management therapy, comprising:
a signal generator to deliver cardiac pacing pulses;
a sensing module to acquire a cardiac electrical signal comprising myocardial depolarization and repolarization signals; and
a processor configured to, responsive to the cardiac electrical signal, detect extracardiac capture due to a cardiac pacing pulse, wherein the sensing module is configured to acquire the cardiac signal for a plurality of paced cardiac cycles, and
the processor is configured to average the cardiac signals acquired for the plurality of paced cardiac cycles to obtain an averaged signal and detect the extracardiac capture from the averaged signal.

8. The system of claim 7, wherein the processor is further configured to determine a cardiac signal template comprising no extracardiac stimulation, and detect the extracardiac capture from a difference between the averaged signal and the template.

9. The system of claim 7, wherein the sensing module is further configured to sense a respiration signal; and
the processor is configured to gate the cardiac electrical signal according to a phase of the respiration signal.

10. The system of claim 7, wherein the processor is configured to adjust a parameter controlling the pacing pulses delivered by the signal generator in response to detecting the extracardiac stimulation.

11. The system of claim 10, wherein the parameter comprises one of a timing parameter and an electrode selection parameter.

12. The system of claim 7, further comprising a communication module to generate an alert notification in response to the processor detecting the extracardiac stimulation.

13. A non-transitory computer-readable medium storing a set of instructions which when implemented in an implantable medical device system cause the system to perform a method for controlling a cardiac rhythm management therapy, the method comprising:
delivering a cardiac pacing pulse;
acquiring a cardiac electrical signal comprising myocardial depolarization and repolarization signals; and
enabling a processor to, responsive to the cardiac electrical signal, detect extracardiac capture due to the cardiac pacing pulse, the method further comprising:
acquiring the cardiac signal for a plurality of paced cardiac cycles;
averaging the cardiac signals acquired for the plurality of paced cardiac cycles to obtain an averaged signal; and
detecting the extracardiac capture from the averaged signal.

* * * * *